United States Patent
Pooch et al.

(10) Patent No.: US 6,652,811 B1
(45) Date of Patent: Nov. 25, 2003

(54) DEVICE FOR MEASURING THE CONCENTRATION OF GASEOUS AND VAPOROUS COMPONENTS OF A GAS MIXTURE

(75) Inventors: Ingo Pooch, Ratekau (DE); Ingo Kaneblei, Ahrensburg (DE)

(73) Assignee: Drägerwerk AG, Lübeck (DE)

( * ) Notice: Subject to any disclaimer, the term of this patent is extended or adjusted under 35 U.S.C. 154(b) by 0 days.

(21) Appl. No.: 08/399,853

(22) Filed: Mar. 7, 1995

(30) Foreign Application Priority Data

May 5, 1994 (DE) .......................... 44 15 866

(51) Int. Cl.[7] .............................................. G01N 21/00
(52) U.S. Cl. .............................. 422/83; 422/85; 422/86; 422/88; 422/55; 436/164; 436/167
(58) Field of Search ............................. 422/83, 85, 86, 422/88, 91, 55–58, 61; 436/164, 167

(56) References Cited

U.S. PATENT DOCUMENTS 5,057,280 A * 10/1991 Stock et al. ................ 422/83
5,089,232 A * 2/1992 May ........................... 422/83
5,397,538 A * 3/1995 Stark et al. ................. 422/83
5,415,838 A * 5/1995 Rieger et al. ............... 422/57

FOREIGN PATENT DOCUMENTS

WO    WO 85/00890    2/1985    ......... G01N/31/22

* cited by examiner

*Primary Examiner*—Lyle A. Alexander
(74) *Attorney, Agent, or Firm*—McGlew and Tuttle, P.C.

(57) ABSTRACT

A device for detecting gaseous and vaporous components of a gas mixture by means of channels 2, which are located next to each other on a support 201, are connected in parallel in terms of flow, and are exposed to the component to be detected along a flow axis 3. A scanning section 6 of a scanning device is provided which extends along one of the channels 2, for detecting the change in color of reaction zones in the channels 2. Multiple channel arrangements can also be analyzed in a simple manner with a scanning section evaluating individual channels. At least some of the channels 2 on the support 201 are directed such that an angle α not equal to 0 is formed between the flow axis 3 and the scanning section 6, and the channels 2 are located in the covered area of the scanning section 6.

16 Claims, 2 Drawing Sheets

DEVICE FOR MEASURING THE CONCENTRATION OF GASEOUS AND VAPOROUS COMPONENTS OF A GAS MIXTURE

FIELD OF THE INVENTION

The present invention pertains to a device for detecting gaseous and vaporous components of a gas mixture by using optically perceptible reaction zones in channels which are located next to one another on a support, are connected in parallel, are arranged between a gas inlet and a gas outlet, and are exposed to the component to be detected along a flow axis following the course of the channel, and with a scanning section of a scanning device, which scanning section extends along at least one of the channels.

BACKGROUND OF THE INVENTION

A device of the above-described type has become known from DE-C39,02,402. In the prior-art device, channels extending in parallel on a chip-like support are provided, wherein gas can flow through the channels from a gas inlet to a gas outlet, and on the inside, which acts as a reaction zone, the channels contain a substance which reacts with the component to be detected. The gas flows through the channels along a flow axis that follows the course of the channel and covers the gas inlet and the gas outlet in an aligned manner.

The individual channels may be connected in parallel in terms of flow to make possible the simultaneous detection of the individual components of the gas mixture. To evaluate the change in color, which has taken place in the individual channels due to the reaction of the substance with the component to be detected, the support is pushed into an optoelectronic scanning device, which makes possible the scanning of the length of the layer whose color has changed in the individual channels. The individual channels are brought one after another into the range of action of the optoelectronic scanning device by means of feed rollers, with which a displacing movement of the support is performed, and they are evaluated. The optoelectronic scanning device is designed essentially such that individual LEDs with corresponding detectors, e.g., 6 LEDs, with which the length of the zone whose color has changed is determined, are arranged along the flow axis of the channel to be evaluated. Channels connected in parallel are frequently used when the composition of the gas mixture is unknown, and the type of the substance of the individual components must first be determined. The concentration of the components in the gas sample is initially of secondary importance here.

If such an analysis is to be performed with the prior-art device, the individual channels, which already have the optically detectable reaction zones as a consequence of the parallel admission of the gas, must be brought one after another into the range of action of the optoelectronic by means of the feed rollers. This increases the time needed for the evaluation. Even though it would be possible to simultaneously evaluate even more channels by installing additional LEDs, which are arranged in a matrix-like pattern, this would lead to a disproportionate increase in the price of the optoelectronic scanning device, especially because the additional LEDs are not needed during the evaluation of a single channel.

A device for detecting gaseous components, in which individual capsules, which are filled with detection substance and are activated before the beginning of the measurement, has become known from WO 85/00890. The components to be detected enter the interior of the capsules by diffusion and engage in a chemical reaction that can be evaluated with an optoelectronic detection device with the detection substance. Three capsules, which are arranged in parallel and next to one another on the support, can be simultaneously evaluated with the optoelectronic detection device. The reaction of the component to be detected with the detection substance takes place in the capsules due to diffusion of the component into the interior of the capsule. Flow of the component to be detected through individual capsules from a gas inlet to a gas outlet is not provided and is also not possible, because the detection substance occurs as a liquid, which completely fills the capsule.

SUMMARY AND OBJECTS OF THE INVENTION

The primary object of the present invention is to improve a device of the class described such that multi-channel arrangements connected in parallel in terms of flow can also be analyzed in a simple manner with an optoelectronic scanning device that evaluates single channels along a scanning section.

This object is attained by the channels being aligned on the support such that an angle a not equal to zero is formed between the flow axis and the scanning section, and the channels are located in the covered area of the scanning section.

The advantage of the present invention is essentially the fact that due to the channels being arranged at an angle to the detection section, the channels can be simultaneously evaluated within the covered area with a scanning section, and so-called spot measurements (which are performed to determine whether or not a certain component or certain components is/are present in the gas sample) can thus be performed in a particularly simple manner. The channels are arranged in the covered area of the scanning section such that they are always in the active area of the scanning section. If the scanning section consists of, e.g., 6 LEDs for scanning the change in the color of the reaction zones, six channels crossing the scanning section can also be evaluated if these are arranged within the range of action of one LED. The channels can be etched or milled into the support, or they may be designed as a film pack with individual channels or as capillary tubes, in which case, e.g., the capillary tubes are placed into the support. The advantage of a simultaneous evaluation of a plurality of channels for the user is the fact that information on the type of the composition of the gas sample to be investigated can be obtained by a single measurement after a short measurement time, without the support having to be moved within the detection device. Once the substance being sought is identified, the substance can subsequently be quantitatively analyzed by a one-channel measurement, i.e., with a channel extending along the scanning section.

The channels are preferably arranged in a radial pattern on the support, and the channels may originate from a reference point on the support. In the case of the radial arrangement, the angle a between the flow axis and the scanning section is, in general, different from one channel to the next.

The channels may also be arranged in parallel to one another on the support, and an especially simple, advantageous arrangement is obtained by directing the channels at right angles to the scanning section.

The channels are preferably arranged on the support such that the scanning section is located approximately at half the length L of the channels. A change in the color of the reaction zone within one channel extending over at least half the length of the channel can be thus be detected. However, depending on the task, it is also possible to arrange the channels on the support such that the scanning section is located more in the area of the beginning or the end of the channel, wherein the beginning of the channel is defined as the point of inlet of the gas sample to be analyzed into the channel.

Sections of the channels are advantageously bent in the direction of the scanning section. The length of the section is preferably selected to be such that it is located at least between two active sections of the scanning section. If the active sections consist of individual LEDs, the length of the section is at least the distance between two LEDs along the scanning section.

If the scanning device consists of individual optical channels, e.g., an LED array of 6 LEDs, and two LEDs are needed for the evaluation of one section, three channels can be simultaneously evaluated.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF FIG. 1.

Figure 1:
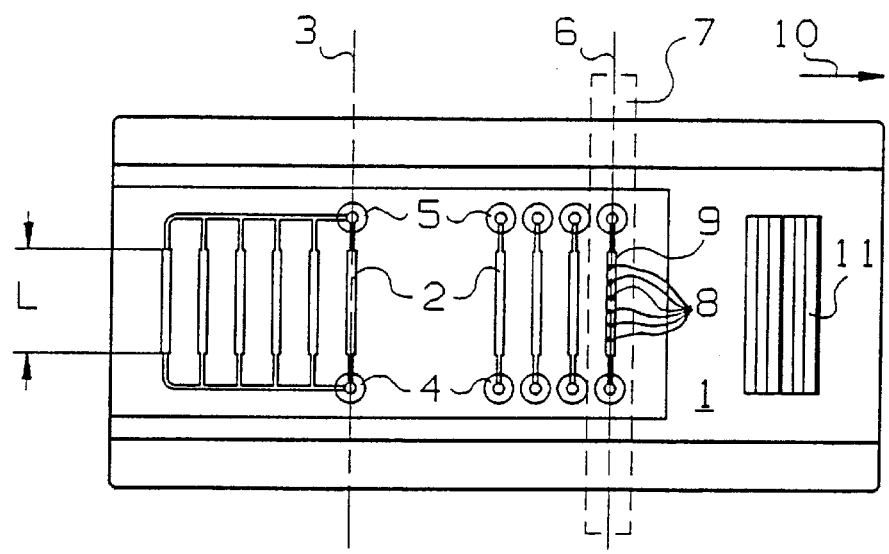
FIG. 1 is a top view of a support with a multiple arrangement of channels according to the state of the art.

FIG. 1 shows a plate-like, chip-like support 1 with a multiple arrangement of channels 2 according to the state of the art, through which gas flows along a flow axis 3 from a gas inlet 4 to a gas outlet 5. For the sake of greater clarity, FIG. 1 shows only one flow axis 3. The channels 2 have reaction zones 9, which extend within the channels 2 along the flow axis 3 and whose color changes under the action of the component to be detected. The change in color is detected with an optoelectronic scanning device 7, which is illustrated in FIG. 1 only schematically by a dotted line. The individual channels 2 in the embodiment shown are to be brought one after another into the range of action of the optoelectronic scanning device 7, whose optical part consists essentially of an LED array 8 extending along a scanning section 6. The LED array 8 is illustrated in FIG. 1 in the form of 6 discrete points, which represent an LED each, and by means of which the change in color of the reaction zone 9 is locally measured in the direction of the flow axis 3 of the channel 2 to be investigated. Such an optoelectronic scanning device 7 is described in, e.g., German Patent No. DE-PS 26,28,790.

The displacing movement of the support 1 is performed by means of feed rollers, not shown in FIG. 1, along the arrow 10. An optoelectronic scanning device for the support 1 with individual channels 2 is illustrated as a block diagram in DE-PS 39,02,402. The type and the number of the channels 2 included are coded by means of a bar code field 11 on the support 1. The first four channels 2 on the support 1 are used for the individual detection of certain components, by allowing a gas sample to be analyzed to flow individually through the channels 2 from the gas inlet 4 to the gas outlet 5 and by the change in color of the reaction zone 9 of each channel 2 being recorded by the optoelectronic scanning device 7. The rear six channels 2 on the support 1 are connected in parallel in terms of flow, i.e., they have only one common gas inlet 4 and gas outlet 5. After the admission of gas to the rear six channels 2, the optoelectronic scanning device 7 must be aligned with each of the six channels 2 one after another in order to evaluate the change in color of the reaction zones 9 present in the channels 2. Such a parallel admission of gas into the channels 2 is performed, e.g., in the case of so-called spot measurements, when an unknown component in a gas mixture is to be qualitatively analyzed, but a quantitative measurement is not yet necessary.

Detailed of Description of the Preferred Embodiment.

Figure 2:
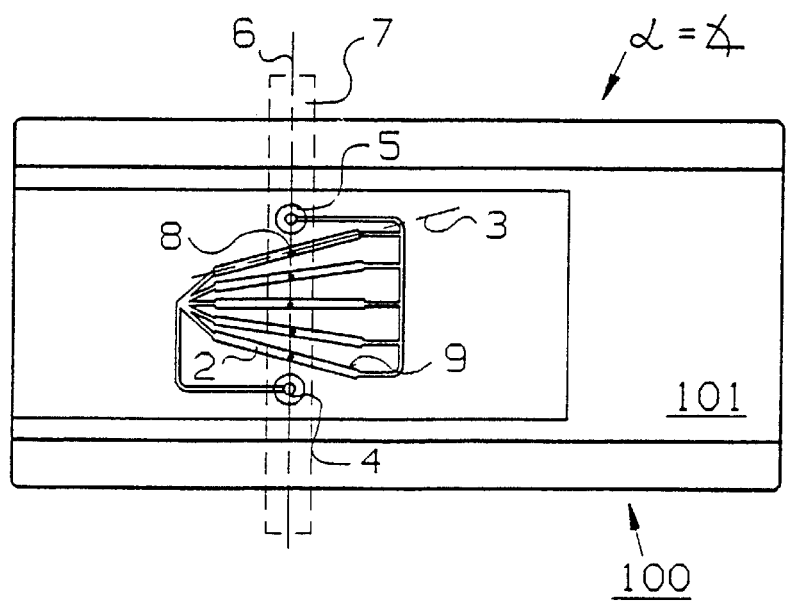
FIG. 2 is a view similar to FIG. 1, showing a first multiple arrangement of channels on a support, according to the invention.

FIG. 2 shows a first multiple arrangement 100 of channels 2 on a support 101, which are connected in parallel in terms of flow, and through which gas flows from the gas inlet 4 to the gas outlet 5. The difference from the channel arrangement according to FIG. 1 is that the flow axes 3 of the channels 2 form an angle α with the scanning section 6, as a result of which all channels 2 are simultaneously located in the range of action of the optoelectronic scanning device 7 with the LED array 8 along the scanning section 6, namely along a scanning section line and whether a change in color of one of the reaction zones 9 is present can be determined by a single measurement cycle. In FIG. 2, the channels 2 are arranged in a radial pattern on the support 101. Identical components are designated by the same reference numbers as in FIG. 1.

Figure 3:
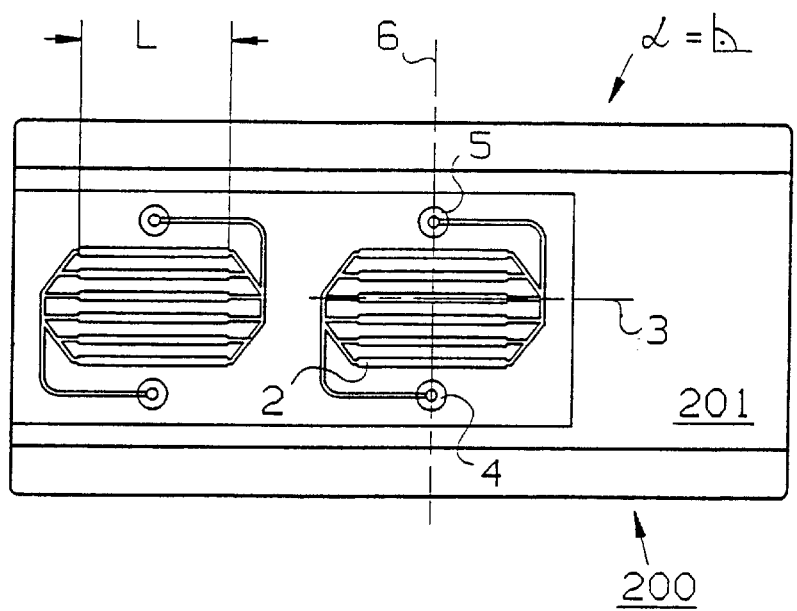
FIG. 3 is a view similar to FIG. 1 of a second multiple arrangement of channels on a support, according to the invention.

FIG. 3 shows a second multiple arrangement 200 of channels 2 on a support 201, in which the channels 2 are aligned in parallel on the support 201, and the flow axes 3 of the channels 2 are at right angles to the scanning section 6. Identical components are designated by the same reference numbers as in FIGS. 1 and 2.

Figure 4:
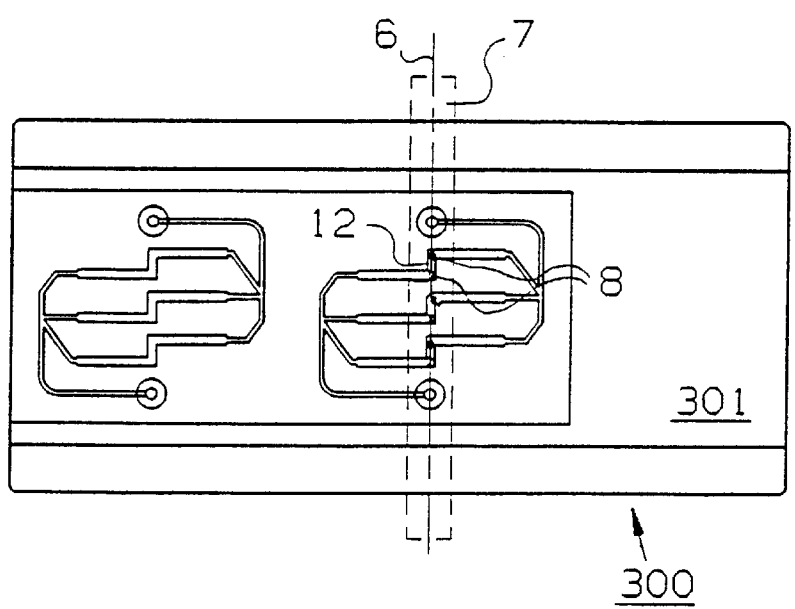
FIG. 4 is an alternative course of the channels of the arrangement according to FIG. 3.

FIG. 4 shows a third multiple arrangement 300 of three channels 2 on a support 301, in which sections 12 of the channels 2 are bent in the direction of the scanning section 6, in deviation from FIG. 3. The lengths of the sections 12 are selected to be such that the sections are covered by two light-emitting diodes of the LED array 8, as a result of which a quantitative measurement is also possible, to a certain extent, besides a qualitative evaluation. Three channels 2 can be simultaneously evaluated with an LED array 8 of six light-emitting diodes, and additional measurement steps that would otherwise be necessary are eliminated due to the possibility of a simultaneous quantitative measurement.

While specific embodiments of the invention have been shown and described in detail to illustrate the application of the principles of the invention, it will be understood that the invention may be embodied otherwise without departing from such principles.

What is claimed is:

1. A device for detecting gaseous and vaporous components of a gas mixture, comprising: channel means for defining optically perceptible reaction zones, said channel means including channels, each zone being inside a channel;

a support for said channels, each channel having a gas inlet and a gas outlet for parallel gas flow, each of said channels having a flow axis following a course of said channel; a scanning device having a scanning section, at least two of said channels being arranged to define an angle, not equal to zero, formed between said flow axis and said scanning section, each of said channels being located in a position with a channel portion covered by said scanning section.

2. Device according to claim 1, wherein said channels are arranged in a radial pattern on said support.

3. Device according to claim 1, wherein said angle equals 90 degrees.

4. Device according to claim 1, wherein said channels are arranged in parallel to one another on said support.

5. Device according to claim 4, wherein said angle is equal to 90 degrees.

6. Device according to claim 1, wherein said scanning section is located approximately at a location which is half a length of said channels.

7. Device according to claim 1, wherein said sections of said channels are bent in a direction of said scanning section.

8. A device according to claim 1, wherein said scanning section includes a plurality of LED elements provided in an array, extending substantially along a line, one LED element being provided for a corresponding one of said plurality of channels, with a portion of said one of said channels disposed between said support and said LED element.

9. A device for detecting gaseous and vaporous components of a gas mixture, comprising:

a support;

a plurality of channels, each channel being connected to said support and each channel having a gas inlet and a gas outlet for parallel gas flow, each of said channels having a flow axis following a course of said channel;

a scanning device with a scanning section extending along a scanning section line, said scanning section being disposed facing said support with at least a portion of each of said plurality of channels being disposed between said support and said scanning section, at least some of said plurality of channels being arranged to define an angle, not equal to zero, formed between said flow axis and said scanning section line.

10. A device according to claim 9, wherein said scanning section includes a plurality of LED elements provided in an array, extending substantially along a line, one LED element being provided for a corresponding one of said plurality of channels, with a portion of said one of said plurality of channels disposed between said support and said LED element.

11. A device according to claim 9, wherein said channels are arranged in a radial pattern on said support.

12. A device according to claim 9, wherein said angle is equal to 90°.

13. A device according to claim 9, wherein said channels are arranged in parallel to one another on said support.

14. A device according to claim 9, wherein said scanning section line is disposed at a location with an equal length of each of said channels to each side of said scanning section line.

15. A device according to claim 9, wherein said channels are bent to extend in a direction of said scanning section line.

16. A device for detecting gaseous and vaporous components of a gas mixture, comprising:

a support;

a plurality of channels, each channel being connected to said support and each channel having a gas inlet and a gas outlet for parallel gas flow, each of said channels having a flow axis following a course of said channel;

a scanning device with a scanning section extending along a scanning section line, said scanning section being disposed facing said support with at least a portion of each of said plurality of channels being disposed between said support and said scanning section, at least some of said plurality of channels being arranged to define an angle, not equal to zero, formed between said flow axis and said scanning section line said scanning section including a plurality of LED elements provided in an array, extending substantially along a line, one LED element being provided for a corresponding one of said plurality of channels, with a portion of said one of said plurality of channels disposed between said support and said LED element.

* * * * *